(12) United States Patent
Petralia et al.

(10) Patent No.: US 11,911,190 B2
(45) Date of Patent: Feb. 27, 2024

(54) DEVICE FOR THE RAPID ATTACHMENT OF BIOMEDICAL DEVICES

(71) Applicant: EUROSETS S.R.L., Medolla (IT)

(72) Inventors: Antonio Petralia, Medolla (IT); Nicola Ghelli, Medolla (IT); Paolo Fontanili, Medolla (IT); Alessandro Zerbini, Medolla (IT)

(73) Assignee: EUROSETS S.R.L., Medolla (IT)

( * ) Notice: Subject to any disclaimer, the term of this patent is extended or adjusted under 35 U.S.C. 154(b) by 0 days.

(21) Appl. No.: 17/764,363

(22) PCT Filed: Oct. 2, 2020

(86) PCT No.: PCT/IB2020/059246
§ 371 (c)(1),
(2) Date: Mar. 28, 2022

(87) PCT Pub. No.: WO2021/064659
PCT Pub. Date: Apr. 8, 2021

(65) Prior Publication Data
US 2022/0338949 A1    Oct. 27, 2022

(30) Foreign Application Priority Data
Oct. 2, 2019    (IT) .................. 102019000017732

(51) Int. Cl.
*A61B 50/20*    (2016.01)
*A61B 90/50*    (2016.01)
*A61M 1/16*    (2006.01)

(52) U.S. Cl.
CPC .............. *A61B 50/20* (2016.02); *A61B 90/50* (2016.02); *A61M 1/1698* (2013.01)

(58) Field of Classification Search
CPC ................................ A61B 50/20; A61B 90/50
USPC ....................................... 248/429; 604/93.01
See application file for complete search history.

(56) References Cited

U.S. PATENT DOCUMENTS

| | | | | |
|---|---|---|---|---|
| 5,522,803 | A * | 6/1996 | Teissen-Simony | ... A61M 5/158 604/93.01 |
| 6,056,718 | A * | 5/2000 | Funderburk | ...... A61M 25/0097 604/93.01 |
| 11,547,516 | B2 * | 1/2023 | Schaub | .................. A61B 50/31 |

(Continued)

FOREIGN PATENT DOCUMENTS

| | | |
|---|---|---|
| EP | 2 635 318 A2 | 9/2013 |
| WO | WO 2006/062636 A1 | 6/2006 |
| WO | WO-2006062636 A1 * | 6/2006 ............ A61M 25/02 |

(Continued)

*Primary Examiner* — Todd M Epps
(74) *Attorney, Agent, or Firm* — ASLAN LAW, P.C.

(57) ABSTRACT

A device for the rapid attachment of biomedical devices, comprising: at least one base element associable with a supporting plane and defining a guiding seat extending along a sliding direction, the guiding seat being intended to receive by shifting an anchoring element associable with one or more biomedical devices; removable attachment device/component (or the like) of the base element to the supporting plane; removable locking device/component (or the like) of the anchoring element associated with the base element, the locking device/component locking the anchoring element with respect to the base element along the sliding direction upon reaching a predefined anchoring position.

20 Claims, 5 Drawing Sheets

(56) References Cited

U.S. PATENT DOCUMENTS

2019/0269477 A1    9/2019  Schaub

FOREIGN PATENT DOCUMENTS

| WO | WO 2008/087427 A1 | 7/2008 |
| WO | WO 2012/058778 A2 | 5/2012 |
| WO | WO 2017/100837 A1 | 6/2017 |

* cited by examiner

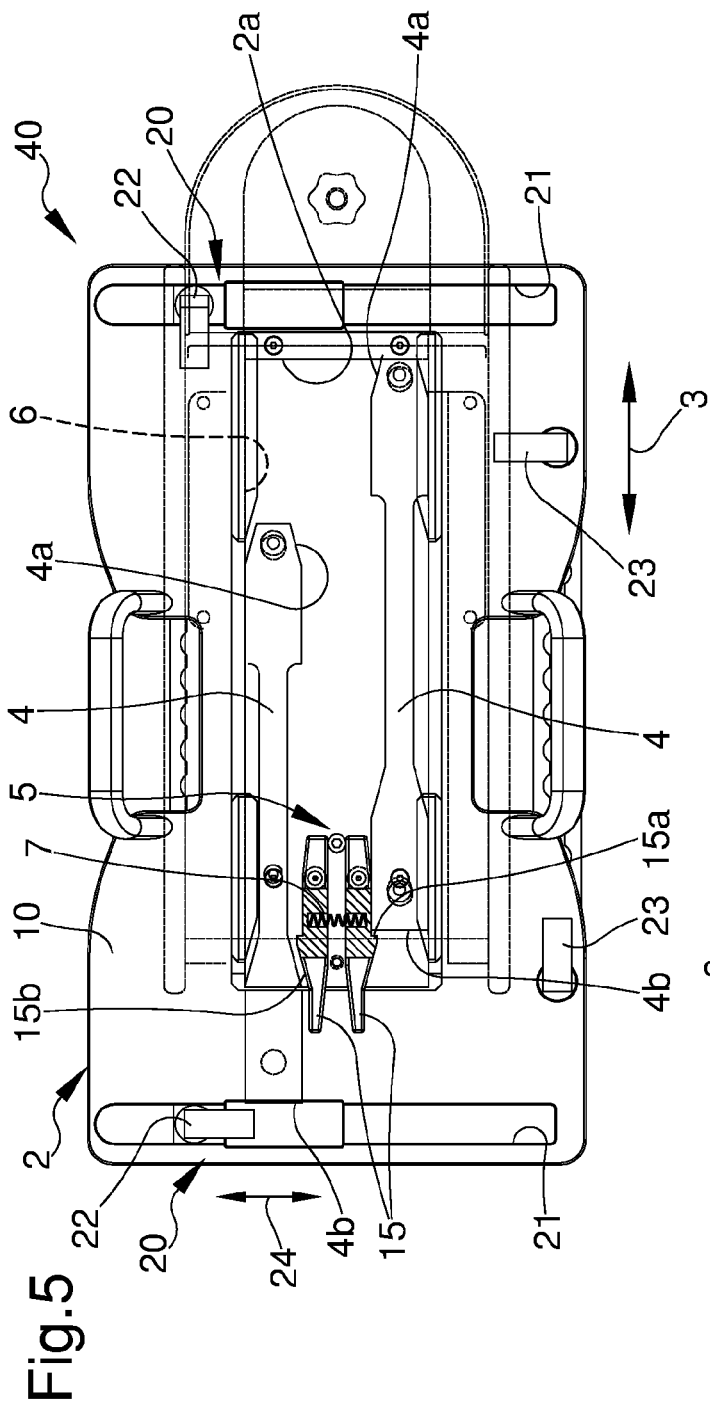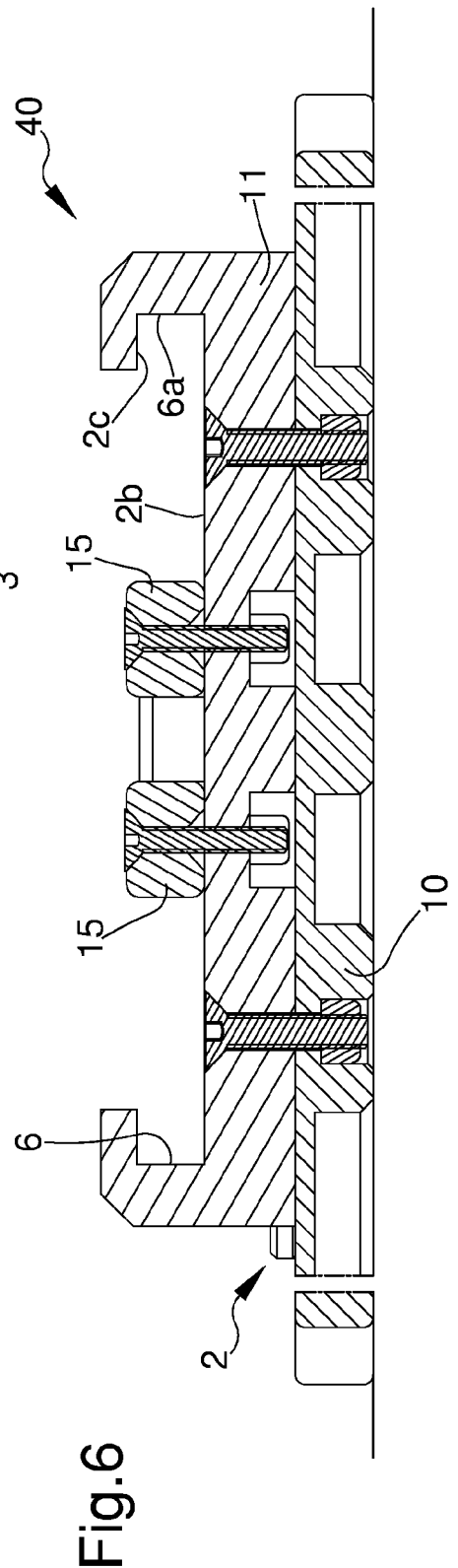

DEVICE FOR THE RAPID ATTACHMENT OF BIOMEDICAL DEVICES

CROSS-REFERENCE TO RELATED APPLICATIONS

This application claims priority to IT Patent Application No. 102019000017732 filed on Oct. 2, 2019, and this application claims priority to and is a 371 of international PCT Application No. PCT/IB2020/059246 filed on Oct. 2, 2020, the entire contents of which are hereby incorporated by reference.

TECHNICAL FIELD

The present invention relates to a device for the rapid attachment of biomedical devices, in particular to medical-healthcare means of transport, such as e.g., vehicles and aircraft.

BACKGROUND ART

Equipment for transport are known, both intra-hospital and extra-hospital, of biomedical devices, such as devices for extracorporeal blood circulation, e.g. oxygenators and centrifugal pumps, or other devices used in hospital practice and in emergency situations.

More in particular, while these devices are widely used in hospital practice, it may also be necessary to use them in emergency situations, such as roadside interventions or in places far from equipped health facilities.

An important aspect of patient healthcare, for example, concerns transport between hospitals, i.e. transport from hospitals with a low level of care to a hospital with a very high level of care. On the one hand, such transport is often a necessary condition for patient survival. On the other hand, however, such transport carries a high risk for the patient himself.

On these occasions, generally characterized by a picture of cardiovascular insufficiency, miniaturized and transportable cardiopulmonary bypass systems are required to provide adequate early treatment.

Perfusion systems used in hospital practice in fact, are not designed for long transport times. In fact, they are generally too large and cumbersome and, therefore, unsuitable to be used in small spaces and under conditions where the time factor, also intended as speed in the preparation of the rescue equipment, is of vital importance.

In addition, these known systems can pose a risk to patient and healthcare personnel safety when used in vehicles and aircraft, often subject to strong positive or negative accelerations. Under these conditions, there is a risk that the equipment used for emergency care may detach and injure the patient or caregivers.

In order to overcome these drawbacks, supporting devices of the perfusion systems have been devised which are adapted to be used on both land and aircraft rescue vehicles.

One of these devices is known from EP 2635318, which describes a supporting plate, which can be fixed to a holding surface, such as the floor of an emergency vehicle, and provided with a plurality of supporting means of the different biomedical devices.

Another device of known type is described by US 2019/0269477.

These known devices do, however, also have some drawbacks.

In fact, their preparation is not easy.

In particular, it takes a long time for healthcare personnel to prepare biomedical devices on the supporting plate.

In addition, if any of the supporting means is damaged or malfunctioning, the relevant biomedical devices may detach from the supporting plate thus compromising the proper operation of the perfusion system.

DESCRIPTION OF THE INVENTION

The main aim of the present invention is to devise a device for the rapid attachment of biomedical devices that allows for the easy and safe attachment of the biomedical devices necessary for care in emergency situations to a means of transport, such as land or air vehicles.

Within this aim, one object of the present invention is to devise a device for the rapid attachment of biomedical devices that allows for an easy preparation by the personnel in charge, in order to reduce the intervention time.

Another object of the present invention is to ensure the safe transport of the biomedical devices, so as to minimize the risk of damage thereto or injury to personnel in charge.

Another object of the present invention is to devise a device for the rapid attachment of biomedical devices that allows overcoming the above mentioned drawbacks of the prior art in a simple, rational, easy, effective to use and low cost solution.

The above mentioned objects are achieved by the present device for the rapid attachment of biomedical devices according to claim 1.

The objects are also achieved by the present piece of equipment for the rapid attachment of the biomedical devices according to claim 18.

BRIEF DESCRIPTION OF THE DRAWINGS

Other characteristics and advantages of the present invention will be more evident from the description of a preferred, but not exclusive, embodiment of a device and a piece of equipment for the rapid attachment of biomedical devices, illustrated by way of an indicative, yet non-limiting example, in the attached tables of drawings in which:

FIG. 5 is a plan view from above of the device in FIG. 3;

FIG. 6 is a sectional view of the device in FIG. 5.

EMBODIMENTS OF THE INVENTION

Figure 1:
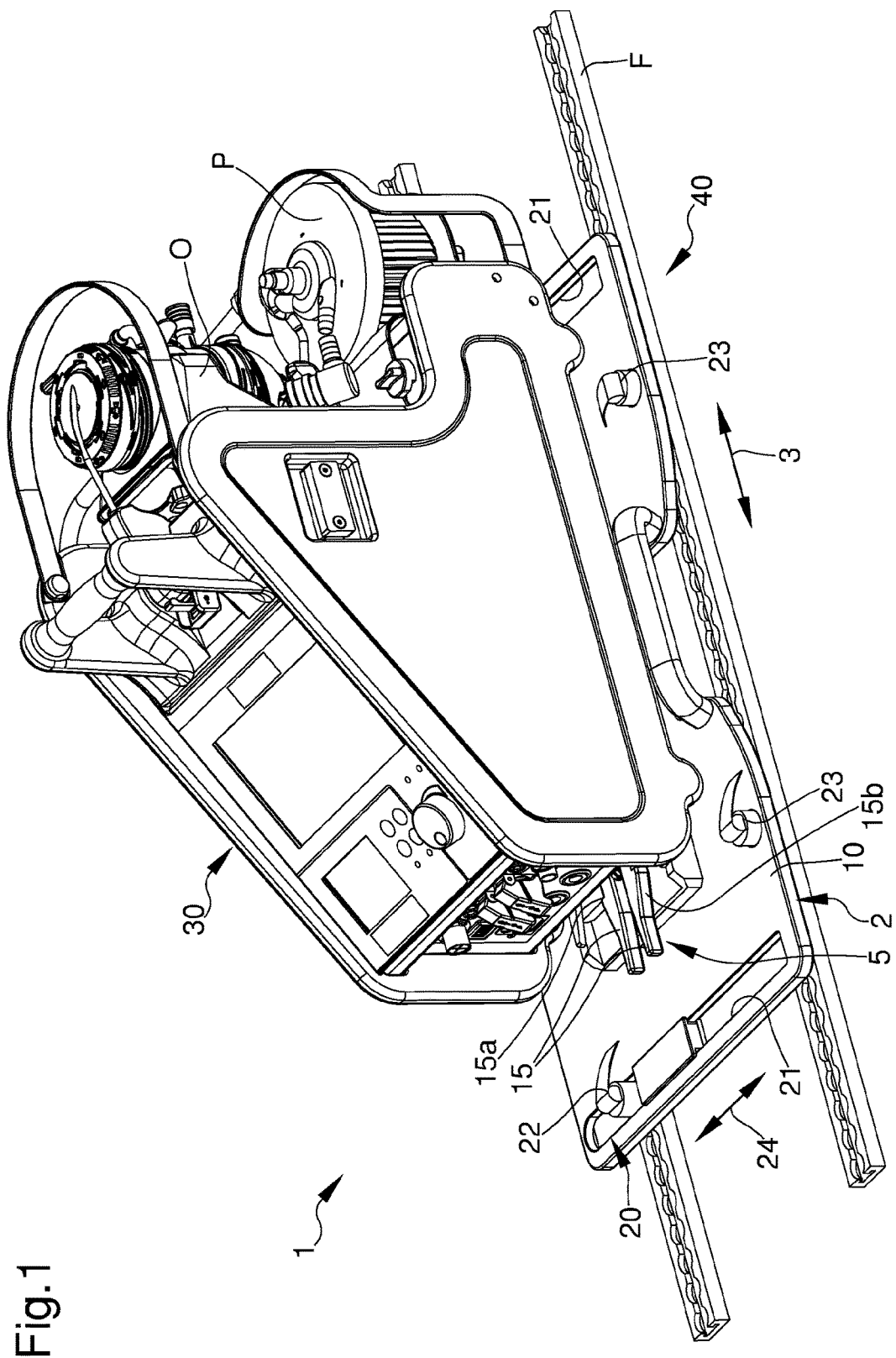
FIG. 1 is an axonometric view of a piece of equipment according to the invention.

With particular reference to these figures, reference numeral 1 globally indicates a piece of equipment for the rapid attachment of biomedical devices and reference numeral 40 globally indicates a device for the rapid attachment of biomedical devices, in particular to medical-healthcare means of transport.

According to the invention, the device 40 comprises a base element 2 associable with a supporting plane S and defining a guiding seat 6 extending along a sliding direction 3.

The equipment 1 comprises, therefore, the device 40 and at least one anchoring element 4 associable with one or more biomedical devices O, P and insertable by shifting in the guiding seat 6 along the sliding direction 3.

The biomedical devices O, P comprise, e.g., an oxygenator O and the relevant pumping assembly P for extracorporeal blood circulation, which are associated with a piece of equipment for the support of biomedical devices 30. The anchoring element 4 is, in turn, associated with the equipment for the support of biomedical devices 30 at the point where its bottom wall is located by means of relevant fastening members, e.g. of the threaded type.

In the embodiment shown in the figures, the base element 2 comprises a load-bearing element 10, associable with the supporting plane S and a guiding element 11, which is locked together with the load-bearing element 10 and defining the guiding seat 6.

The supporting plane S consists e.g. of the floor of a transport vehicle, such as an ambulance, helicopter or other motorized rescue vehicles.

Appropriately, the equipment 1 comprises removable attachment means 20,23 of the base element 2 to the supporting plane S.

More specifically, the attachment means 20,23 comprise first attachment means 20 movable along a direction of adjustment identified in the figures with the double arrow 24. The first attachment means 20 comprise one or more slots 21 that run along the direction of adjustment 24 and one or more engagement elements 22 inserted sliding inside the slots 21 to lock the base element 2 together with the supporting plane S. Preferably, the direction of adjustment 24 is arranged transversely to the sliding direction 3.

In the embodiment shown in the figures, the slots 21 are defined on the load-bearing element 10.

Since on the supporting plane S of emergency transport vehicles, such as ambulances, rescue helicopters and the like, attachment bars F are generally fitted, the mutual distance of which may vary depending on the situation, the engagement elements 22 are made to slide along the slots 21 so as to adapt to the position of the attachment bars mentioned above.

The attachment bars F extend along the sliding direction 3 and are arranged substantially parallel to each other.

Therefore, in order to allow the engagement with the attachment bars F, the slots 21 extend along a direction which is transverse to the sliding direction 3.

Advantageously, the attachment means 20 also comprise second attachment means 23 to the supporting plane S, e.g. of the type of additional engagement elements that can be moved manually between an engagement position and a release position. The second attachment means 23 are attached with respect to the base element 2. In the embodiment shown in the figures, the second attachment means 23 are also associated with the load-bearing element 10.

Still according to the invention, the device 40 comprises removable locking means 5 of the anchoring element 4 associated with the base element 2, where the locking means 5 are adapted to prevent the anchoring element 4 from displacing with respect to the base element 2 along the sliding direction 3 upon reaching a predefined anchoring position. The predefined anchoring position corresponds, e.g., to the end-of-stroke position of the anchoring element 4 on the base element 2. In particular, the base element 2 has a stop surface 2a and the predefined anchoring position corresponds to the position taken by the anchoring element 4 when resting against the stop surface 2a.

At the same time, the guiding seat 6 is shaped in such a way that it prevents the anchoring element 4 from lifting.

Advantageously, the base element 2 defines at least one holding surface 2b adapted to support the anchoring element 4 and at least one anchoring surface 2c facing the holding surface 2b and adapted, in use, to prevent the anchoring element 4 from lifting with respect to the base element 2.

More in detail, the guiding seat 6 is substantially C-shaped and is delimited below and above by the holding surface 2b and by the anchoring surface 2c, respectively.

In other words, the anchoring element 4 is adapted to engage by shifting with the base element 2 along the sliding direction 3 by inserting itself inside the guiding seat 6. The guiding seat 6 also defines a lateral containment wall 6a arranged adjacent and transverse to the anchoring surface 2c.

In the embodiment shown in the figures, the locking means 5 are associated with the guiding element 11, which defines the stop surface 2a, the holding surface 2b and the anchoring surface 2c and is adapted to engage with the anchoring element 4.

Preferably, the locking means 5 comprise at least one locking element 15 movable between a locking position, wherein it is adapted to interact with the anchoring element 4 to prevent it from displacing along the sliding direction 3, and a release position, wherein it allows the anchoring element 4 to be displaced along the sliding direction 3.

Conveniently, the locking means 5 comprise elastic means 7 adapted to counteract the displacement of the locking element 15 from the locking position to the release position.

More specifically, the locking element 15 is adapted to displace from the locking position to the release position as a result of the sliding of the anchoring element 4 towards the predefined anchoring position and is adapted to displace, as a result of the action of the elastic means 7, from the release position to the locking position as a result of the reaching of the predefined anchoring position. The locking element 15 is therefore pushed to the release position as a result of the interaction with the anchoring element 4 during its forward movement to the predefined anchoring position, while it displaces independently to the locking position when the anchoring element 4 reaches this predefined anchoring position.

Advantageously, the locking element 15 has at least one locking surface 15a adapted to interact with the anchoring element 4 in the predefined anchoring position, so as to prevent it from displacing along the sliding direction 3 and at least one contact surface 15b positioned inclined with respect to the sliding direction 3 and adapted to interact with the anchoring element 4 during the displacement thereof close to the predefined anchoring position; the locking element 15 is therefore adapted to displace from the locking position to the release position as a result of the interaction of the anchoring element 4 with the contact surface 15b.

More specifically, as a result of the interaction of the anchoring element 4 with the locking element 15, a force is generated having a transverse component with respect to the sliding direction 3 which causes the compression of the elastic means 7.

Figure 2:
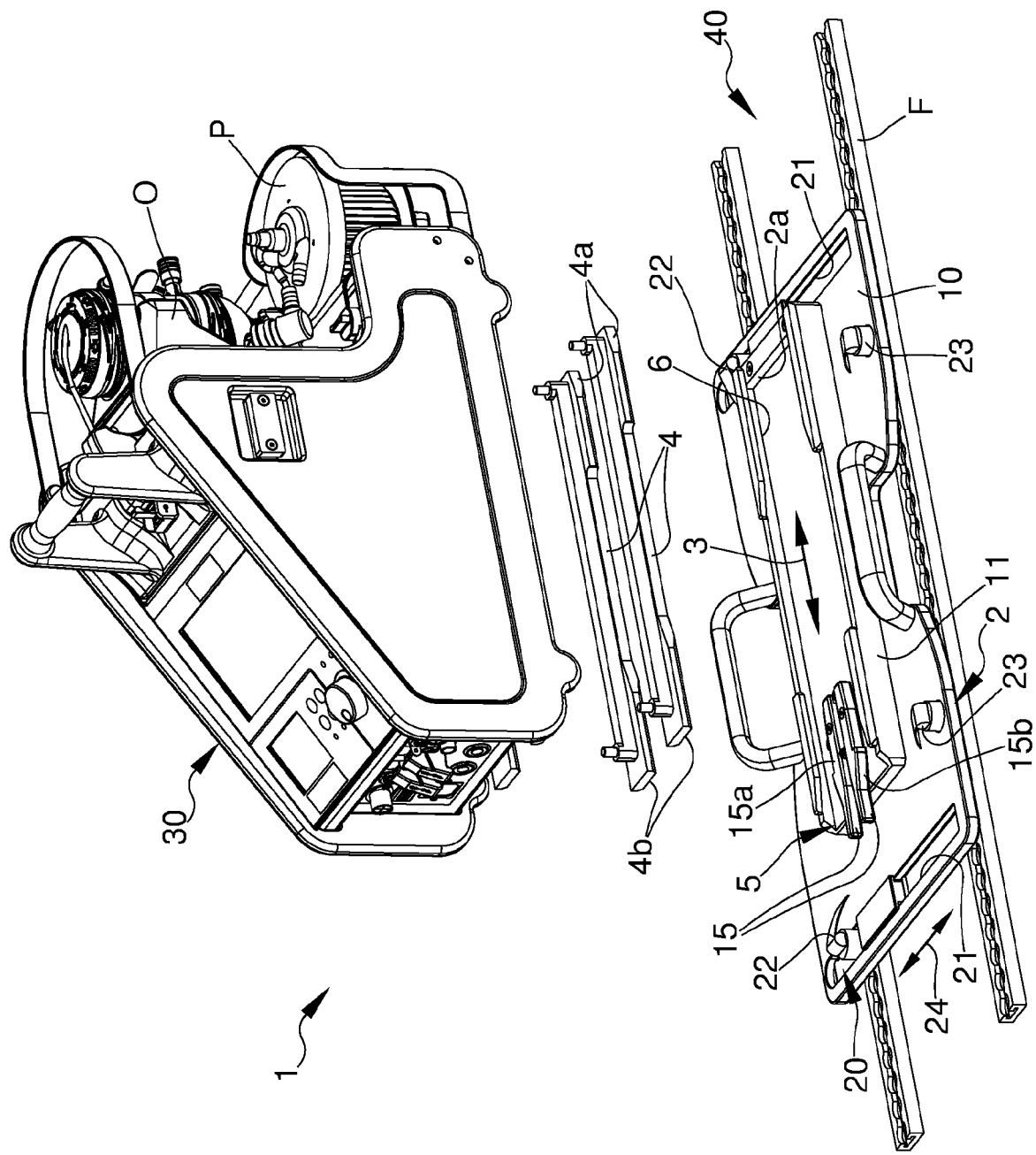
FIG. 2 is an exploded view of the equipment in FIG. 1.
Figure 3:
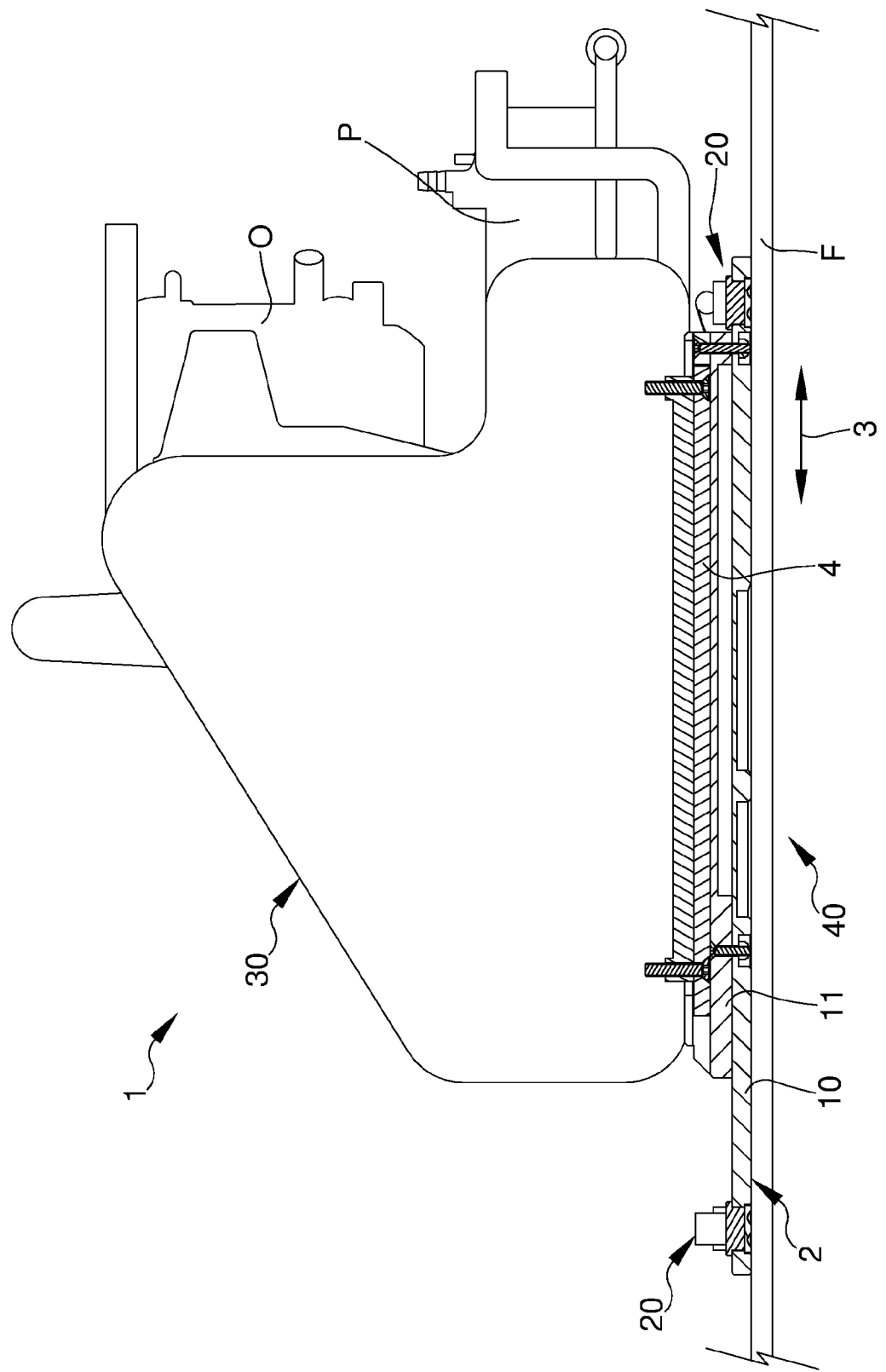
FIG. 3 is a side sectional view of the equipment in FIG. 1.
Figure 4:
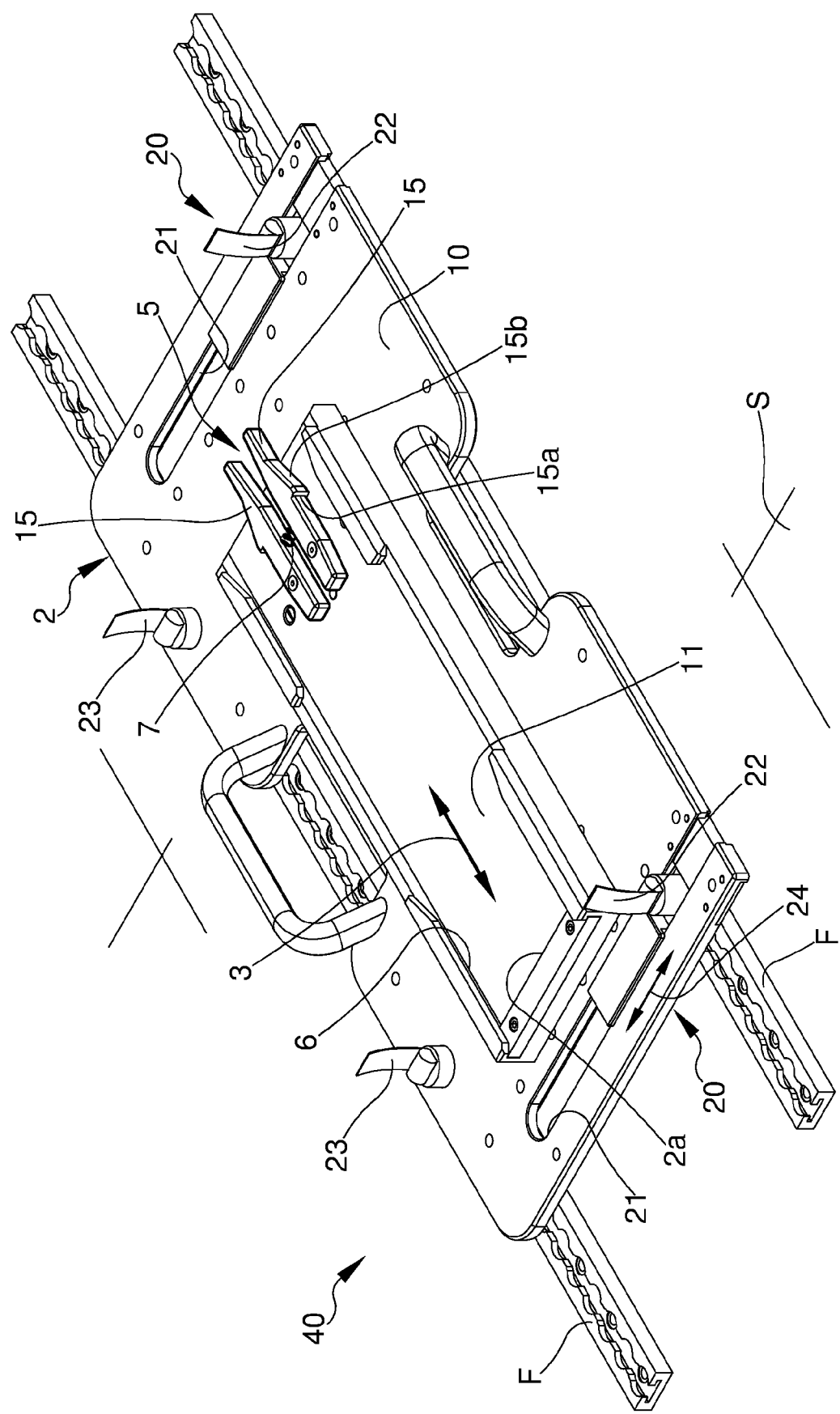
FIG. 4 is an axonometric view of a device according to the invention.

As shown in FIGS. 2 and 5, the anchoring element 4 has, in turn, at least a first end portion 4a and a second end portion 4b opposite each other. The first end portion 4a is adapted to interact, during its shift along the sliding direction 3 inside the guiding seat 6, with the contact surface 15b to displace the locking element 15 from the locking position to the release position. The second end portion 4b is adapted to interact, in the predefined anchoring position, with the locking surface 15a to prevent the anchoring element itself from displacing along the sliding direction 3, away from the stop surface 2a.

Advantageously, the locking means 15 comprise at least two locking elements 15, which are spaced away from each other in the locking position with respect to the release position. The elastic means 7 are positioned between the locking elements 15 and are adapted to push them to the corresponding locking positions.

Appropriately, the contact surfaces 15b of the locking elements 15 are arranged in such a way that they diverge from each other outwards moving close to the predefined anchoring position.

In this embodiment, the equipment 1 comprises two anchoring elements 4 arranged spaced away from each other transversely with respect to the sliding direction 3.

More particularly, the locking elements 15 are positioned, in use (i.e. during the forward movement of the anchoring elements 4 along the sliding direction 3 and in the predefined anchoring position), between the anchoring elements 4.

The operation of the present invention is as follows.

First of all, the base element 2 is attached to the supporting plane S using the attachment means 20,23. In particular, once the load-bearing element 10 is arranged above the attachment bars F described above, the position of the engagement elements 22 is adjusted along the slots 21 so that they are brought to the attachment bars themselves and then the mutual engagement is carried out.

After the engagement elements 22 have been attached to the attachment bars F, the additional attachment elements 23 are also attached.

Then, the equipment for the support of biomedical devices 30 is attached to the anchoring element 4 and the latter to the base element 2.

More in detail, after the anchoring elements 4 applied on the bottom of the equipment for the support of biomedical devices 30 are aligned to the guiding element 11, the anchoring elements themselves are moved forward along the sliding direction 3. The anchoring elements 4 interact with the relevant first end portions 4a with the locking elements 15, and in particular with the relevant contact surfaces 15b, by displacing them from the locking position to the release position. After the anchoring elements 4 reach the predefined anchoring position (defined by the stop surface 2a), the locking elements 15 automatically displace, as a result of the action of the elastic means 7, to the locking position, where the relevant locking surface 15a interacts with the second end portion 4b of the corresponding anchoring element 4 and prevents it from displacing along the sliding direction 3. The stop surface 2a in turn prevents the anchoring elements 4 from sliding further along the sliding direction 3. At the same time, the anchoring surface 2c prevents the anchoring elements 4 from lifting.

If it is necessary to remove or move the biomedical devices O, P with respect to the base element 2, the locking elements 15 are manually displaced from the locking position to the release position so that the anchoring elements 4 can be moved along the sliding direction 3 away from the predefined anchoring position, i.e. away from the stop surface 2a.

It has in practice been ascertained that the described invention achieves the intended objects and in particular the fact is underlined that the equipment to which the present invention relates allows attaching in a practical and easy way, thanks to the conformation of the guiding element and of the locking means, the biomedical devices required to carry out the cardiovascular assistance in emergency situations to a rescue transport vehicle, whether of land or aerial type.

In particular, the anchoring surface and the locking means allow the operators in charge to attach the biomedical devices to the guiding element in an extremely fast and safe manner, thus allowing to prepare in a short time the necessary equipment for the rescue and its safe transport. At the same time, the locking means devised allow them to be quickly removed for use on a stretcher or a hospital bed.

The invention claimed is:

1. A device for the rapid attachment of biomedical devices, said device comprising:
   at least one base element associable with a supporting plane and defining a guiding seat extending along a sliding direction, said guiding seat being intended to receive by shifting an anchoring element associable with one or more biomedical devices;
   removable attachment means of said base element to the supporting plane;
   removable locking means of said anchoring element associated with said base element, said locking means locking said anchoring element with respect to said base element along said sliding direction upon reaching a predefined anchoring position,
   wherein said base element has a stop surface positioned transversely to said sliding direction and intended to interact with said anchoring element to define said predefined anchoring position.

2. The device according to claim 1, wherein said base element defines at least one holding surface adapted to support said anchoring element and at least one anchoring surface facing said holding surface and adapted, in use, to prevent said anchoring element from lifting with respect to said base element.

3. The device according to claim 2, wherein said guiding seat is substantially C-shaped and is delimited above by said anchoring surface.

4. The device according to claim 2, wherein said base element comprises at least one supporting element associable with the supporting plane and at least one guiding element which is locked together with said supporting element and defining said sliding direction, said guiding element defining said holding surface and said anchoring surface, and said locking means being associated with the guiding element.

5. A device for the rapid attachment of biomedical devices, said device comprising:
   at least one base element associable with a supporting plane and defining a guiding seat extending along a sliding direction, said guiding seat being intended to receive by shifting an anchoring element associable with one or more biomedical device;
   removable attachment means of said base element to the supporting plane;
   removable locking means of said anchoring element associated with said base element, said locking means locking said anchoring element with respect to said base element along said sliding direction upon reaching a predefined anchoring position,
   wherein said locking means comprise at least one locking element movable between a locking position, wherein said locking means is adapted to interact with said anchoring element to prevent said locking means from displacing along said sliding direction, and a release position, wherein said locking means allows said anchoring element to be displaced along said sliding direction.

6. The device according to claim 5, wherein said locking means comprise elastic means adapted to counteract the displacement of said locking element from the locking position to the release position.

7. The device according to claim 6, wherein said locking element is adapted to displace from the locking position to the release position as a result of the sliding of said anchoring element towards said predefined anchoring position and is adapted to displace, as a result of the action of said elastic means, from the release position to the locking position as a result of the reaching of said predefined anchoring position.

8. The device according to claim 5, wherein said locking element has at least one locking surface adapted to interact with said anchoring element in the predefined anchoring position to prevent said locking element from displacing along said sliding direction and at least one contact surface positioned inclined with respect to said sliding direction and adapted to interact with said anchoring element during the displacement thereof close to the predefined anchoring position, said locking element displacing from the locking position to the release position as a result of the interaction of said anchoring element with said contact surface.

9. The device according to claim 8, wherein the contact surfaces of said locking elements are arranged in such a way that the contact surfaces diverge from each other outwards moving close to the predefined anchoring position.

10. The device according to claim 5, wherein said locking means comprise at least two of said locking elements, which are spaced away from each other in the locking position with respect to the release position.

11. The device according to claim 10, wherein said elastic means are positioned between said locking elements.

12. A device, for the rapid attachment of biomedical devices, said device comprising
    at least one base element associable with a supporting plane and defining a guiding seat extending along a sliding direction, said guiding seat being intended to receive by shifting an anchoring element associable with one or more biomedical devices;
    removable attachment means of said base element to the supporting plane;
    removable locking means of said anchoring element associated with said base element, said locking means locking said anchoring element with respect to said base element along said sliding direction upon reaching a predefined anchoring position;
    removable attachment means of said base element to the supporting plane.

13. The device according to claim 12, wherein said attachment means comprise at least first attachment means movable along a direction of adjustment.

14. The device according to claim 13, wherein said first attachment means comprise one or more slots extending along said direction of adjustment and one or more engagement elements inserted sliding inside said slots to lock said base element together with said supporting plane.

15. The device according to claim 13, wherein said direction of adjustment is transverse to said sliding direction.

16. The device according to claim 12, wherein said attachment means comprise at least second attachment means the position of which is fixed with respect to said base element.

17. Equipment for the rapid attachment of biomedical devices, said equipment comprising:
    at least one device for the rapid attachment according to claim 1;
    at least one anchoring element associable with one or more biomedical devices and engageable by shifting in said guiding seat along said sliding direction to lock the relevant biomedical device with respect to said base element.

18. The equipment according to claim 17, wherein said anchoring element has at least a first end portion intended to interact, when shifts along said sliding direction, with said contact surface to displace said locking element from the locking position to the release position, and at least a second end portion, opposite said first end portion, adapted to interact, in the predefined anchoring position, with said locking surface to prevent the anchoring element from displacing along said sliding direction.

19. The equipment according to claim 17, further comprising: two of said anchoring elements arranged spaced away from each other transversely with respect to said sliding direction.

20. The equipment according to claim 18, wherein said locking elements are positioned, in use, between said anchoring elements.

* * * * *